(12) United States Patent
Soukup

(10) Patent No.: US 6,755,794 B2
(45) Date of Patent: Jun. 29, 2004

(54) ADJUSTABLE STYLET

(75) Inventor: Thomas Soukup, Plymouth, MN (US)

(73) Assignee: Synovis Life Technologies, Inc., St. Paul, MN (US)

( * ) Notice: Subject to any disclaimer, the term of this patent is extended or adjusted under 35 U.S.C. 154(b) by 0 days.

(21) Appl. No.: 09/843,040

(22) Filed: Apr. 25, 2001

(65) Prior Publication Data

US 2002/0004638 A1 Jan. 10, 2002

Related U.S. Application Data

(60) Provisional application No. 60/199,428, filed on Apr. 25, 2000.

(51) Int. Cl.$^7$ ............................ A61B 6/00; A61M 25/00
(52) U.S. Cl. ........................................ 600/585; 600/435
(58) Field of Search ................................. 600/433–435, 600/585; 604/170.02, 164.13, 523, 525, 526

(56) References Cited

U.S. PATENT DOCUMENTS

| | | | |
|---|---|---|---|
| 2,118,631 A | | 5/1938 | Wappler |
| 3,789,841 A | * | 2/1974 | Antoshkiw ................. 128/2.05 |
| 3,802,440 A | | 4/1974 | Salem et al. |
| 3,841,308 A | | 10/1974 | Tate |
| 4,209,019 A | | 6/1980 | Dutcher et al. |
| 4,215,703 A | | 8/1980 | Willson |
| 4,271,845 A | | 6/1981 | Chikashige et al. |
| 4,456,017 A | | 6/1984 | Miles |
| 4,719,924 A | | 1/1988 | Crittenden et al. |
| 4,757,827 A | | 7/1988 | Buchbinder et al. |
| 4,759,748 A | | 7/1988 | Reed |
| 4,822,345 A | | 4/1989 | Danforth |
| 4,846,174 A | | 7/1989 | Willard et al. |
| 4,869,719 A | * | 9/1989 | Hogan ........................ 604/174 |
| 4,886,067 A | | 12/1989 | Palermo |
| 5,060,660 A | | 10/1991 | Gambale et al. |
| 5,151,105 A | * | 9/1992 | Kwan-Gett ..................... 623/1 |
| RE34,086 E | * | 10/1992 | George ......................... 128/200 |
| 5,282,478 A | | 2/1994 | Fleischhaker, Jr. et al. |
| 5,304,131 A | | 4/1994 | Paskar |
| 5,315,996 A | | 5/1994 | Lundquist |
| 5,322,064 A | | 6/1994 | Lundquist |
| 5,327,906 A | | 7/1994 | Fideler |
| 5,338,301 A | | 8/1994 | Diaz |
| 5,341,817 A | | 8/1994 | Viera |

(List continued on next page.)

FOREIGN PATENT DOCUMENTS

| WO | WO94/27666 | 12/1994 |
|---|---|---|
| WO | WO 00/22981 | 4/2000 |

OTHER PUBLICATIONS

*Medtronic Placer™ Model 6232 Steerable Stylet*, Premarket Notification document, Medtronic, Inc., 4 pgs.; Jun. 16, 2000.
*Medtronic Eupalamus Deflectable Stylet*, Premarket Notification document, Medtronic, Inc., 8 pgs.; Oct. 18, 2000.
Web site print–out: *New Implantation Tool, Steerable Stylet Clinical Assessment Study*, Fikru Maru, Joachim Kreutzer, Rolf Pieper, Peter Steen Hansen, Peter Zwicky, Mariette Schönbeck, Thomas Vesterlund, HeartWeb Organization, vol. 4, No. 1, Article No. 98110008, 8 pgs.; Nov. 1998.

*Primary Examiner*—Eduardo C. Robert
*Assistant Examiner*—Anuradha Ramana
(74) *Attorney, Agent, or Firm*—Fredrikson & Byron, P.A.

(57) ABSTRACT

An adjustable stylet includes a core wire having a portion surrounded by a compression member preferably comprised of a flat wire spring. Depending upon the configuration, compression or relaxation of the compression member in response to forces at the tip or handle of the stylet results in adjustments to the characteristics of the stylet. In a first embodiment, the stiffness of the stylet is adjustable. In a second embodiment, the length of the stylet is adjustable. In a third embodiment, both the stiffness and the length of the stylet are adjustable.

41 Claims, 7 Drawing Sheets

U.S. PATENT DOCUMENTS

| | | |
|---|---|---|
| 5,396,902 A | 3/1995 | Brennen et al. |
| 5,437,288 A | 8/1995 | Schwartz et al. |
| 5,439,006 A | 8/1995 | Brennen et al. |
| 5,441,483 A | 8/1995 | Avitall |
| 5,480,382 A * | 1/1996 | Hammerslag et al. ........ 604/95 |
| 5,573,520 A | 11/1996 | Schwartz et al. |
| 5,605,162 A | 2/1997 | Mirzaee et al. |
| 5,605,543 A | 2/1997 | Swanson |
| 5,662,119 A | 9/1997 | Brennen et al. |
| 5,674,271 A | 10/1997 | Denker |
| 5,726,615 A | 3/1998 | Bloom |
| 5,752,915 A | 5/1998 | Neubauer et al. |
| 5,758,656 A | 6/1998 | Schroeder |
| 5,762,615 A | 6/1998 | Weier |
| 5,820,591 A | 10/1998 | Thompson et al. |
| 5,824,031 A | 10/1998 | Cookston et al. |
| 5,833,632 A | 11/1998 | Jacobsen et al. |
| 5,851,203 A | 12/1998 | van Muiden |
| 5,873,842 A | 2/1999 | Brennan et al. |
| 5,916,178 A | 6/1999 | Noone et al. |
| 5,938,623 A | 8/1999 | Quiachon et al. |
| 5,957,903 A | 9/1999 | Mirzaee et al. |
| 6,004,279 A | 12/1999 | Crowley et al. |
| 6,017,319 A | 1/2000 | Jacobsen et al. |
| 6,027,462 A | 2/2000 | Greene et al. |
| 6,039,743 A | 3/2000 | Quiachon et al. |
| 6,048,339 A | 4/2000 | Zirps et al. |
| 6,059,739 A | 5/2000 | Baumann |
| 6,068,623 A | 5/2000 | Zadno-Azizi et al. |
| 6,113,557 A * | 9/2000 | Fagan et al. ................. 600/585 |
| 6,132,390 A | 10/2000 | Cookston et al. |
| 6,152,931 A * | 11/2000 | Nadal et al. ................. 606/108 |
| 6,183,420 B1 | 2/2001 | Douk et al. |
| 6,203,506 B1 | 3/2001 | Boström |

* cited by examiner

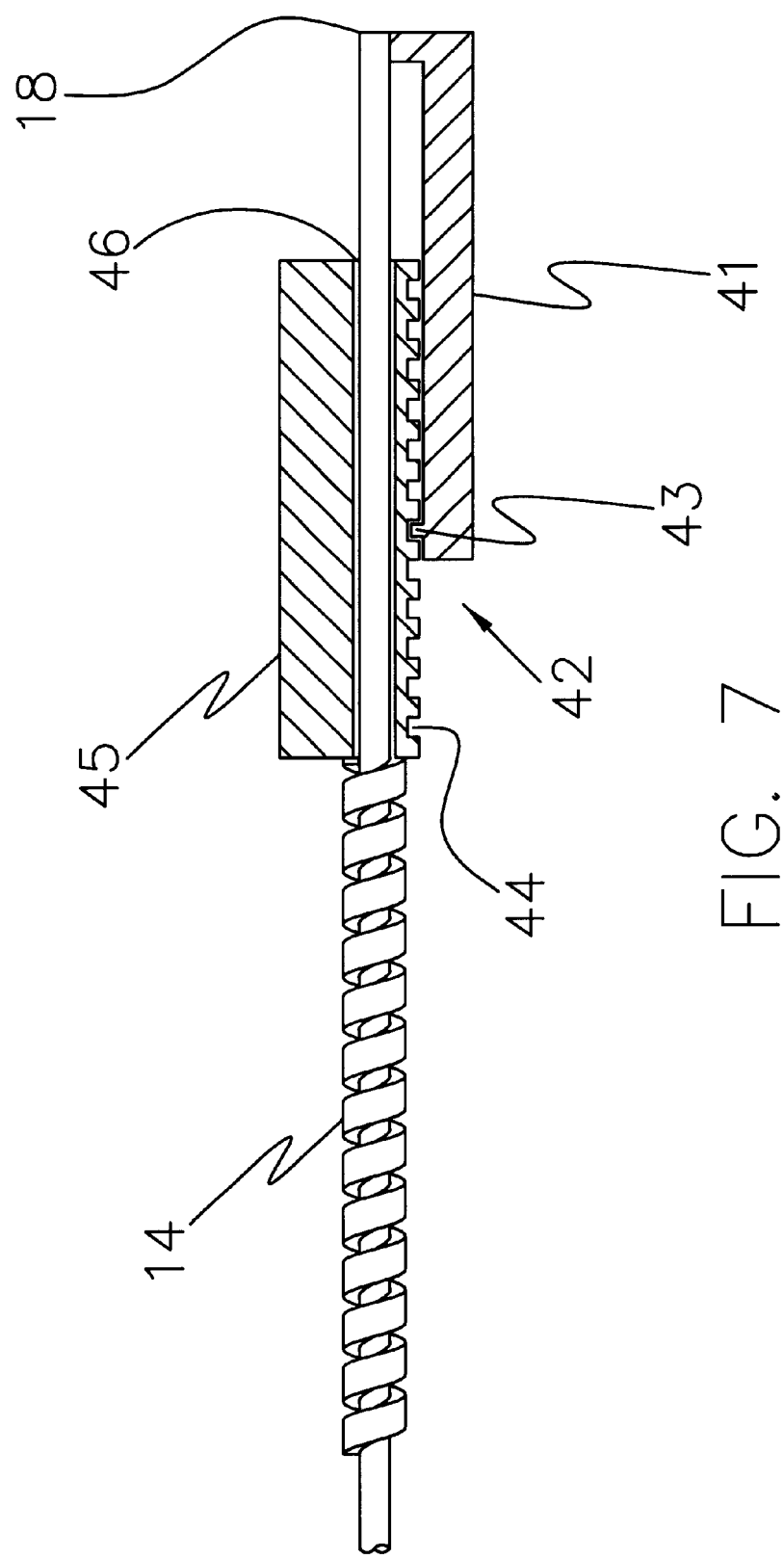

ADJUSTABLE STYLET

This application claims the benefit of U.S. Provisional Application No. 60/199,428 filed Apr. 25, 2000.

FIELD OF THE INVENTION

The present invention relates generally to the field of intravascular leads and catheters. More specifically, the present invention relates to an adjustable stylet for use in positioning such leads and catheters.

BACKGROUND OF THE INVENTION

Stylets and guidewires are used to control the manner in which intravascular leads and catheters are introduced into the veins or arteries of the body. Although both kinds of devices are often thought of as simply very small wires, the purpose and operation of stylets is significantly different as compared to guidewires.

Conventional intravascular procedures typically involve an initial step of introducing and routing a guidewire through a patient's vascular system to provide a rail or track along which additional intravascular devices may be introduced. Once a guidewire is in place, a sheath is routed over at least a portion of the guidewire to provide a larger opening into the vein or artery and sometimes to protect the inside walls of the vessels along the route of the guidewire. With the sheath in place, the guidewire may be removed or may remain in place as additional intravascular devices such as intravascular leads and catheters are introduced into the patient's vascular system.

To better accomplish the purpose of a guidewire of providing a track along the patient's vascular system for other intravascular devices, it is desirable that the guidewire have a region at the tip of the guidewire, referred to as the distal end, that is extremely flexible. Preferably, the guidewire has the ability to vary the flexibility of the distal tip and/or deflect the distal tip so as to aid in routing the guidewire through the patient's vascular system. U.S. Pat. Nos. 4,215,703, 4,456,017, 4,719,924, 4,886,067 and 5,060,660 describe designs for guidewires that use an internal tensioning member or pull wire to alter the characteristics of the non-expandable distal tip and/or to deflect the distal tip. U.S. Pat. Nos. 4,271,845 4,822,345, 5,605,162, 5,762,615, 5,851,203, 5,957,903 and 6,183,420 describe various designs for guidewires with adjustable stiffness by moving a core member axially within the distal region of the guidewire. U.S. Pat. Nos. 5,938,623 and 6,039,743 describe a guidewire with adjustable stiffness that is controlled by running electricity through a memory metal wire tip. U.S. Pat. No. 5,341,817 describes a guidewire extension arrangement in which a smaller inner extension can be pushed out of a larger core segment to extend the distal end of the guidewire. U.S. Pat. Nos. 4,846,174 and 5,338,301 describe guidewires with a core member that can be extended to axially stretch an angioplasty balloon at the distal tip. In a similar manner, U.S. Pat. Nos. 3,841,308 and 4,759,748 describe catheters that utilize a core member to axially stretch a coiled section at the distal end of the catheter for purposes of controlling delivery of a fluid.

In contrast to the guidewire which serves as a track over which other intravascular devices are routed, a stylet is used within an internal lumen of an intravascular device both to push that device through the vascular system and to steer the device as it is being pushed. Although some intravascular devices are designed to steer themselves using internal pull wires, almost all leads, most catheters and some guidewires have an inner channel or lumen into which a stylet is inserted. In addition to pushing the intravascular device through the vascular system by engaging the distal end of the device, the stylet also serves to deflect the distal end of the intravascular device so as to steer the distal end through the vascular system. Unlike the lead, catheter or guidewire, which has a distal region that is flexible and floppy, the stylet must be stiffer and more rigid so as to enable the stylet to push the lead or catheter through the patient's vascular system. Conventionally, stylets having different bends on the distal end are used at different points of advancing the lead or catheter to a desired location. For straight segments of a vessel a straight stylet is used, whereas a stylet with a curved distal tip is used to navigate the lead or catheter through a curved portion of a vessel. U.S. Pat. No. 2,118,631 shows an early stylet formed of coils of flat wire welded to plugs at both ends that could be bent by the physician into either a straight or curved configuration at its distal end prior to insertion into the lumen of a catheter or the like. In a more recent type of stylet, an operator controls the direction of deflection of the tip of the stylet while it is in place in the lumen, which in turn controls the direction of the cardiac lead or catheter as it is moved along the veins or arteries. An example of a stylet with such a deflecting tip is shown in U.S. Pat. No. 5,824,031. Other examples of steerable stylets can be found in U.S. Pat. No. 5,873,842 and PCT Publ. No. WO 00/22981.

The more control and flexibility an operator has over an intravascular device, the easier it is to operate that device. In the case of stylets, the physical demands of engaging the distal end of a lumen of an intravascular device so as to push that device through the vascular system impose constraints on the beam strength of the device that are much different than the constraints encountered for a guidewire, catheter or lead. Most guidewires are constructed from a tapered core wire with a coiled round wire wrapped around this tapered core wire in order to achieve the necessary flexibility in the distal region of the guidewire. Stylets, on the other hand, are generally constructed of a solid wire of uniform diameter without any coils around this wire in order to achieve the necessary strength and rigidity required over the entire length of the device so as to function as a stylet. Because of these differences, the techniques for improving control and flexibility that have been utilized for guidewires, catheters and leads are not generally applicable for the design of stylets. It would be desirable to provide for a stylet with improved flexibility and control without the need for changing stylets during a procedure to obtain different orientations of the distal tip of the stylet.

SUMMARY OF THE INVENTION

The present invention is an adjustable stylet. The stylet includes a core wire having a portion surrounded by a compression member preferably comprised of a flat wire spring. Depending upon the configuration, compression or relaxation of the compression member in response to forces at the tip or handle of the stylet results in adjustments to the characteristics of the stylet. In a first embodiment, the stiffness of the stylet is adjustable. In a second embodiment, the length of the stylet is adjustable. In a third embodiment, both the stiffness and the length of the stylet are adjustable.

Unlike most guidewires that are so flexible the guidewire will fall over when grasped only by the ends, the stylet in accordance with the present invention requires a much greater rigidity such that the stylet forms an arc that generally stands up and does not fall over when the stylet is grasped only by the ends. The present invention utilizes a core wire that has a relatively uniform beam strength over its axial length so as to provide the necessary rigidity and strength required for a stylet. The compression member augments the characteristics of the core wire in a manner that is adjustable so as to also be able to more closely emulate the desired characteristics of an adjustable guidewire.

BRIEF DESCRIPTION OF THE DRAWINGS

FIGS. 6 and 7 show cutaway partial sides views of alternate embodiments of the handle for the adjustable stiffness stylet of FIG. 1.

DETAILED DESCRIPTION OF THE PREFERRED EMBODIMENT

Figure 1:
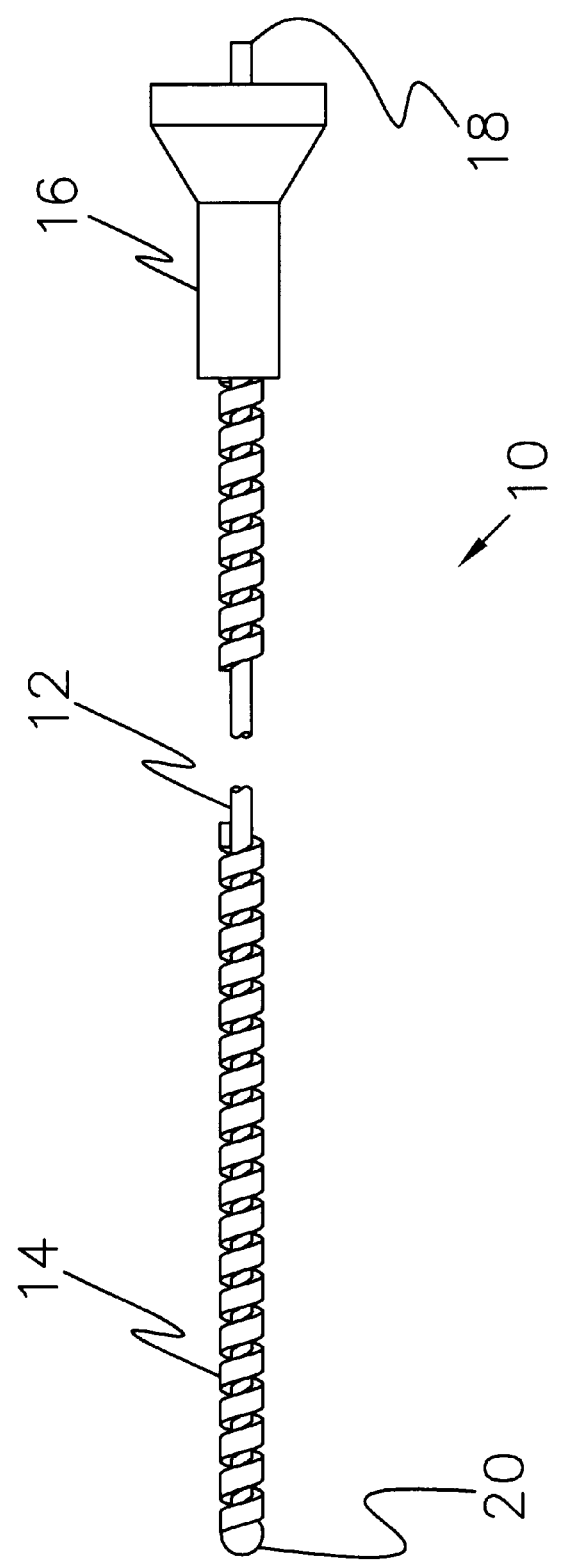
FIG. 1 is a side view of an adjustable stiffness stylet in a relaxed state.

Referring to FIG. 1, an adjustable stiffness stylet 10 comprises a stylet core wire 12, a space wound flat wire spring or compression member 14, a sliding handle 16 located at a proximal end 18 of the core wire 12 and a tip 20 of the core wire 12. Preferably, the compression member 14 is welded, crimped or otherwise secured to the core wire 12 near the tip 20. Preferably, the space wound compression member 14 has an inner diameter (I.D.) that is just slightly larger than the outer diameter (O.D) of the core wire 12. Optionally, a cover tube (not shown) may be secured over the exterior so long as the tube does not interfere with the movement of compression member 14.

Figure 2:
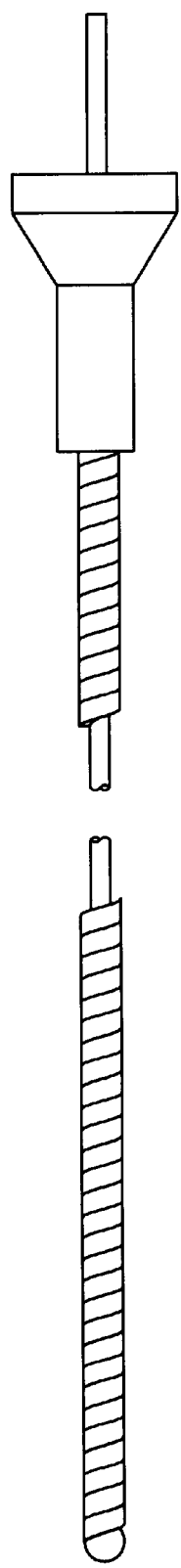
FIG. 2 is a side view of the adjustable stiffness stylet of FIG. 1 in a compressed state.
Figure 6:
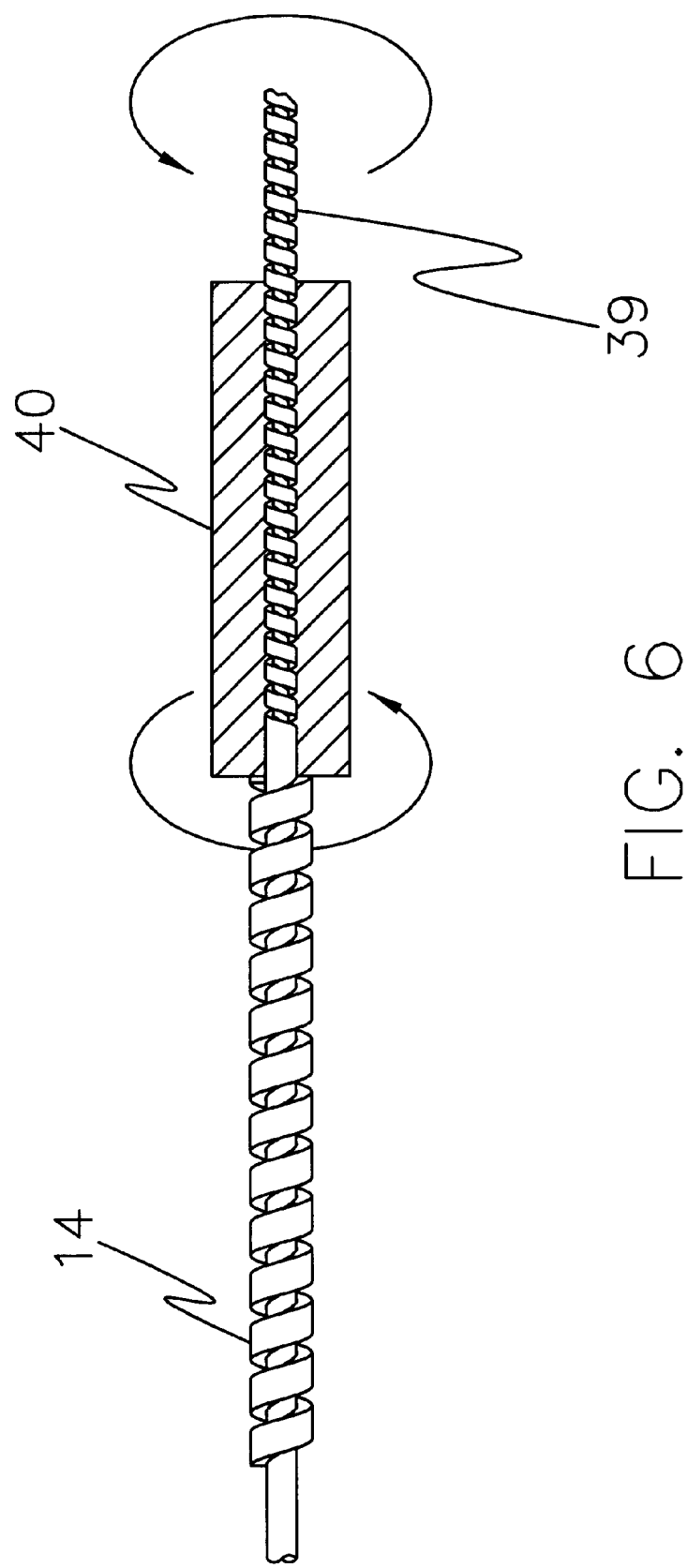

As the sliding handle 16 is pushed toward the tip 20, the handle 16 makes contact with the proximal end of compression member 14 but does not slide over compression member 14. Compression member 14 is compressed in response and the overall flexibility of the stylet 10 begins to stiffen. As more force is applied to the handle 16, the open windings of compression member 14 close and the stiffness of stylet 10 is increased as shown in FIG. 2. When the desired stiffness is achieved, the operator may advance stylet 10 without altering the stiffness by applying force to the proximal end 18 of the core wire 12 without displacing the position of handle 16 relative to the compression member 14. Alternatively, handle 16 may be provided with locking mechanisms to lock the handle 16 in a given position relative to core wire 12, or proximal end 18 of the core wire 12 may be equipped with a separate handle. Handle 16 preferably is slide operated along the longitudinal axis of core wire 12, although it will be understood that handle 16 also could operate in a screw manner (as shown in FIG. 6) or ratchet manner (as shown in FIG. 7) along the longitudinal axis of core wire 12.

Figure 3:
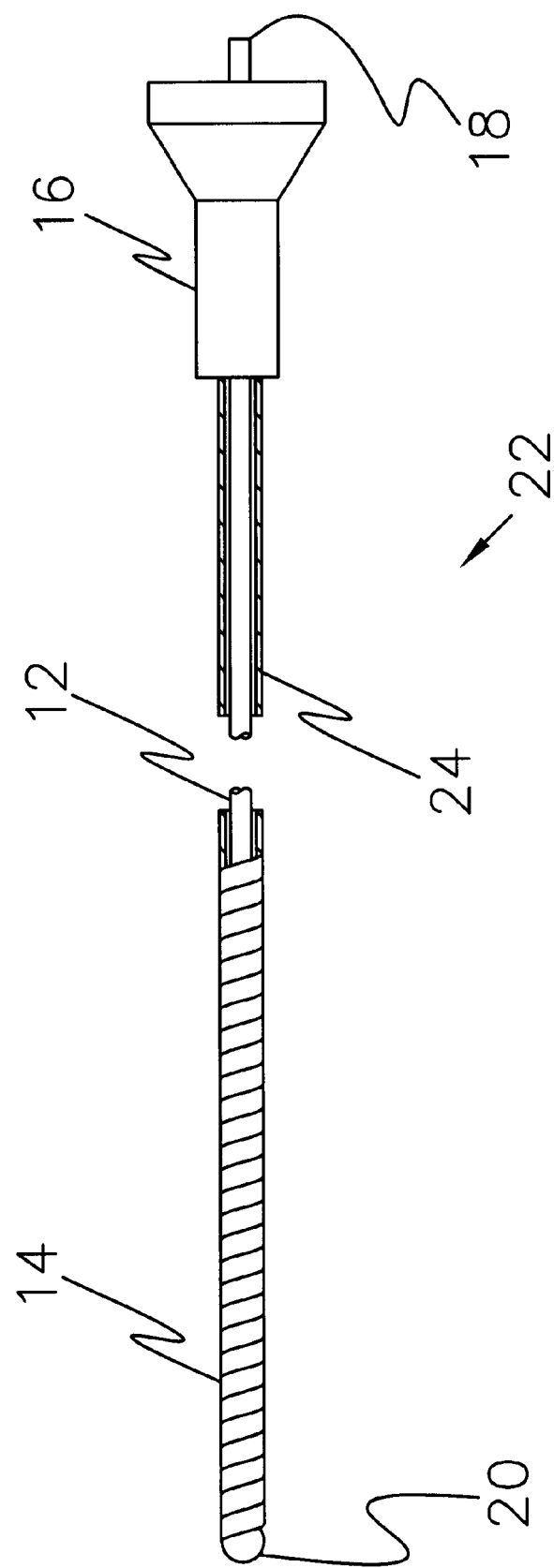
FIG. 3 is a side view of an alternative embodiment of the adjustable stiffness stylet.

FIG. 3 shows an alternate embodiment of an adjustable stylet 22 in which a rigid tube 24 is located between the handle 16 and the compression member 14. In this case, compression member 14 is secured to the tip 20 of the core wire 12 and the resulting stylet has a flexible tip portion corresponding to the length of the core wire 12 surrounded by compression member 14. As the handle 16 is pushed toward the tip 20, the tube 24 is pushed into the proximal end of the compression member 14 and the space wound coils of compression member 14 are compressed, thereby increasing the stiffness of the stylet 22.

Figure 4:
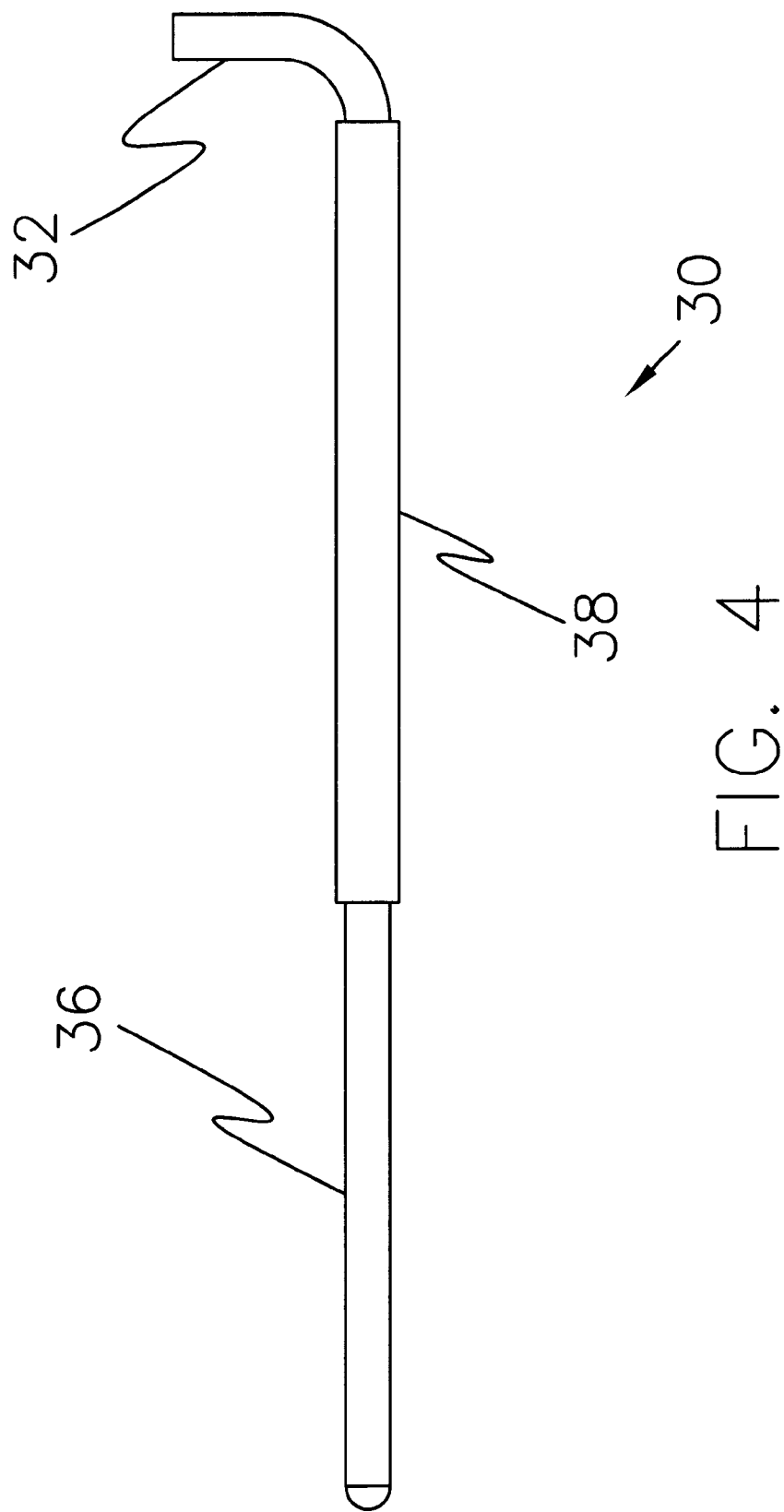
FIG. 4 is a partial side view of an adjustable length stylet.
Figure 5:
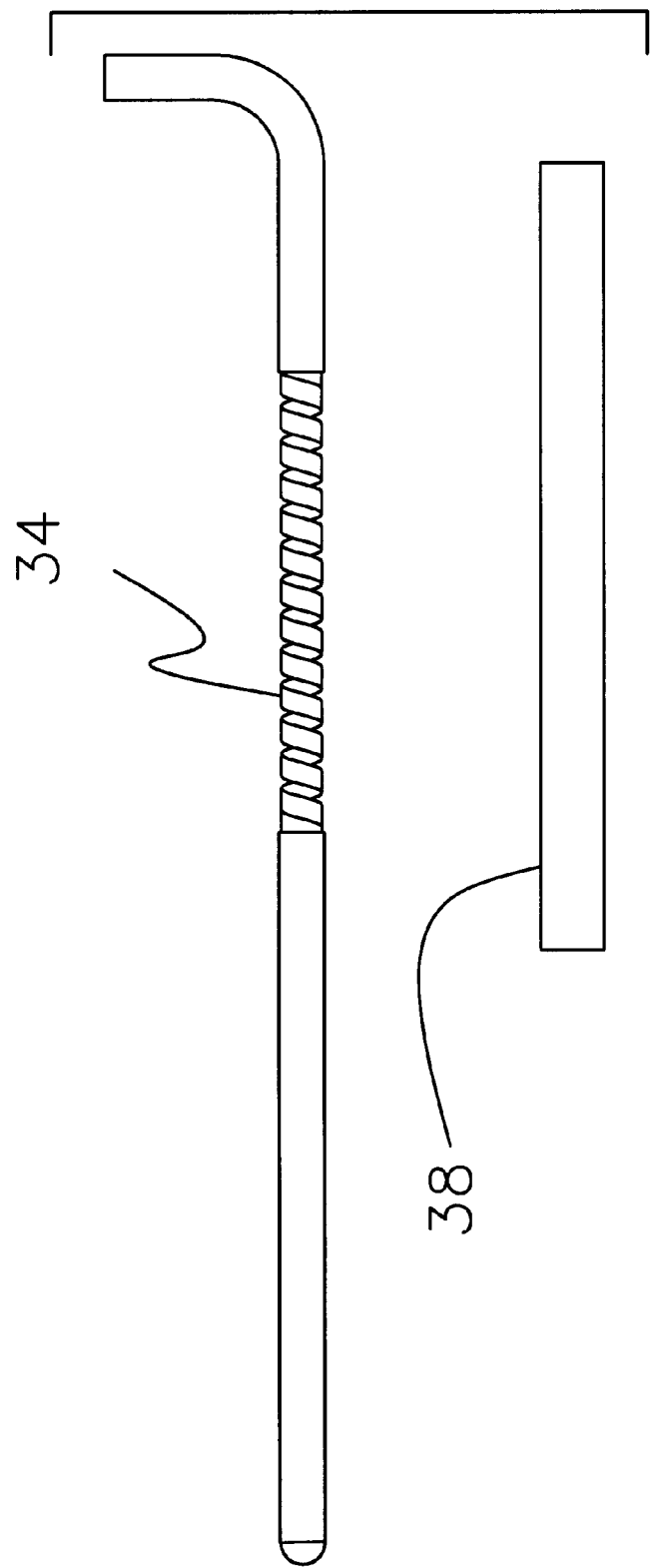
FIG. 5 is a cutaway partial side view of the adjustable length stylet of FIG. 4.

Referring now to FIG. 4, a second embodiment of an adjustable stylet 30 comprises a proximal core wire 32, a compression member 34 (FIG. 5), a distal core wire 36 and a cover tube 38. The cover tube 38 is welded to the proximal core wire 32, but not to the distal core wire 36. The compression member 34 is preferably a space wound flat wire spring that is welded, crimped or otherwise secured to the adjacent ends of the proximal core wire 32 and the distal core wire 36. The stylet core wire is preferably centerless ground at the adjacent ends of the proximal core wire 32 and distal core wire 36 to all several turns of the compression member 34 to be centered on each core wire 32, 36.

Preferably, the distal core wire 36 is relatively short in comparison to the proximal core wire 32, although the lengths of the core wires 32 and 36 may be various lengths. In this embodiment, the compression member 34 is compressed and the overall effective length of the stylet 30 is shortened in response to a compressive force exerted at the distal end of the distal core wire 36. The ability of the stylet 30 to adjust in length reduces the need for stocking and maintaining a variety of different length stylets.

In a third embodiment, the stylet 30 is used as the core wire 12 of the stylet 10 to combine both of the adjustable qualities of the present invention in a single embodiment.

FIGS. 6 and 7 show alternate embodiments for the handle of the adjustable stiffness stylet of FIG. 1 in partial cross-sectional views. In FIG. 6, the proximal end of the stylet core wire 39 is threaded to accept a threaded handle 40. The stiffness of the stylet 10 is increased by compressing the compressive member 14 through turning of the threaded handle 40 clockwise to move the handle 40 away from the threaded proximal end of the stylet core wire 39. Similarly, the stiffness of the stylet 10 may be decreased by decompressing the compressive member 14 through turning the threaded handle 40 counterclockwise toward the threaded proximal end of the stylet core wire 39.

Referring now to FIG. 7, the proximal end 18 of the core wire 12 of the adjustable stiffness stylet 10 is welded or otherwise secured to the bottom part 41 of a multi-piece handle 42 that has a tongue 43. The tongue 43 engages slots 44 of the top part 45 of a multi-piece handle 42, which has an aperture 46 whose inside diameter is slightly larger than the outside diameter of the stylet core wire 12 to allow the stylet core wire 12 to freely slide through the top part 45 of the multi-piece handle 42. The stiffness of the stylet 10 is accomplished through compression of the compressive member 14 by pulling the bottom part 41 of the multi-piece handle 42 toward the proximal end of the core wire 18 in relation to the top part 45 of the multi-piece handle 42. Correspondingly, the stiffness of the stylet 10 can be decreased through relieving compression of the compressive member 14 by pushing the bottom part 41 of the multi-piece handle 42 away from the proximal end of the core wire 18 in relation to the top part 45 of the multi-piece handle 42. Once the desired stiffness of the stylet 10 has be accomplished by placement of the top part 45 and bottom part 41 of the multi-piece handle 42, the tongue 43 on the bottom part 41 engages a slot 44 on the top part 45 of the multi-piece handle 42 to maintain the chosen stiffness.

The core wire 12 is preferably a stainless steel wire having an outer diameter of less than 0.020 inches and preferably in a range between 0.005 and 0.018 inches and in the preferred embodiment approximately 0.014 inches. Above this range, the diameter of the core wire is generally too large to effectively serve as a stylet for insertion in the lumens of most intravascular devices. The physical characteristics of core wire 12 must be suitable for use as a stylet, as opposed to use as a guidewire. Most importantly, the core wire 12 should have a relatively uniform beam strength over its axial length so as to provide the necessary rigidity and strength required for a stylet. By relatively uniform it is understood that manufacturing tolerances or even minor variations in beam strength of less than about +/−10% would be considered relatively uniform in terms of the beam strength of the core wire. The tensile strength of the wire should be at least 150K psi and preferably in a range between 200K psi and 400K psi. Alternative wires suitable for core wire 12 include MP35N, AC10 tungsten, or Nitinol. With existing technologies for wound wire or braided wire, it is not possible to utilize such wires for the core wire 12 in accordance with the present invention because these wires do no exhibit the desired characteristics. As such, the core wire 12 is preferably a solid round wire having a relatively uniform cross-sectional diameter over its axial length.

The compression member 14 is preferably a flat or ribbon wire made of stainless steel or a similar material. The compression member preferably has an aspect ratio of at least 2:1. While the wider cross-sectional dimension of the flat wire can vary anywhere above the lower range of the aspect ratio, preferably the narrow cross-sectional dimension of the flat wire is less than 0.003 inches.

In the embodiment of the adjustable length stylet 30, the principle advantage of this feature is its use in those situations where the length of stylet must be held to very tight tolerances. Typically, the stylet 30 is inserted into an intravascular device within a sterile field prior to insertion in the patient's vascular system with the proximal ends of the stylet 30 and intravascular device locked together with a Luer lock or the like. In some applications, such as neurological applications, the tolerances for the match between the length of the lumen of the intravascular device and the length of the stylet 30 must be within less than 0.010 inches. The ability to adjust the length of the stylet 30 reduces the need for tight tolerance matches between these lengths, thereby affording more interchangeability between stylets and intravascular devices.

What is claimed is:

1. An adjustable stylet for use within a lumen of an intravascular device comprising:

a core wire having a blunt distal end and a proximal end and having an outer diameter of less than 0.020 inches and a relatively uniform beam strength over an axial length of said core wire, said relatively uniform beam strength providing sufficient rigidity for a segment of said axial length to maintain an arc when endpoints of said segment are maintained at a distance less than a length of said segment;

a compression member having a distal end operably secured to said core wire and a proximal end axially movable along said core wire, said compression member comprising a fiat wire space wound around at least a portion of said core wire to form a plurality of successive windings with a wide dimension of said flat wire oriented axially and an axial spacing between successive windings of said compression member;

a handle operably mounted proximate said proximal end of said core wire, said handle axially movable to operably engage said proximal end of said compression member such that said axial spacing between at least a portion of said successive windings is adjusted by movement of said handle, whereby a stiffness of said stylet is adjusted by operation of said handle; and wherein said core wire comprises a first core wire segment and a second core wire segment and a length adjustment member secured between adjacent ends of said first and second core wire segments, said length adjustment member comprising a space wound wire with an axial spacing between successive windings of said length adjustment member such that an axial force applied to at least one end of said length adjustment member decreases said axial spacing between at least a portion of said successive windings of said length adjustment member.

2. The adjustable stylet of claim 1 wherein said compression member is secured to said core wire proximate said blunt distal end of said core wire.

3. The adjustable stylet of claim 1 further comprising a rigid tube member operably positioned around said core wire between said proximal end of said compression member and said handle to transfer axial force applied by said handle to said compression member.

4. The adjustable stylet of claim 1 wherein said flat wire is a stainless steel wire having an aspect ratio of at least 2:1 and having a narrow cross-sectional dimension of less than 0.003 inches.

5. The adjustable stylet of claim 1 wherein said blunt end is comprised of a ball welded to said distal end of said core wire.

6. The adjustable stylet of claim 1 wherein said handle is slidable relative to said core wire.

7. The adjustable stylet of claim 1 wherein said handle includes a handle member secured to said core wire proximate said proximate end of the core wire and a moveable member operably engaged with said handle member such that said moveable member is axially moveable relative to said handle member within a distance determined by said handle member, said moveable member including a proximal portion extending distally beyond said handle member for operably engaging said proximal end of said compression member.

8. The adjustable stylet or claim 7 wherein said moveable member and said handle member include structure such that said moveable member is slidable relative to said handle member.

9. The adjustable stylet of claim 1, wherein said core wire comprises a wire having a uniform cross-sectional diameter.

10. The adjustable stylet of claim 1 wherein said core wire comprises a solid wire.

11. An adjustable stylet for use within a lumen of an intravascular device comprising:

a core wire having a blunt distal end and a proximal end and having an outer diameter of less than 0.020 inches and a relatively uniform beam strength over an axial length of said core wire;

a compression member having a distal end operably secured to said core wire and a proximal end axially movable along said core wire, said compression member comprising a flat wire space wound around at least a portion of said core wire to form a plurality of successive windings with a wide dimension of said flat wire oriented axially and an axial spacing between successive windings of said compression member;

a handle operably mounted proximate said proximal end of said core wire, said handle axially movable to operably engage said proximal end of said compression member such that said axial spacing between at least a portion of said successive windings is adjusted by movement of said handle, whereby a stiffness of said stylet is adjusted by operation of said handle, and wherein said handle includes a handle member secured to said core wire proximate said proximal end of the core wire and a moveable member operably engaged with said handle member such that said moveable member is axially moveable relative to said handle member within a distance determined by said handle member, said moveable member including a proximal portion extending distally beyond said handle member for operably engaging said proximal end of said compression member, wherein said moveable member and said handle member include structure such that said moveable member is screwable relative to said handle member.

12. The adjustable stylet of claim 11 wherein said compression member is a flat stainless steel wire having an aspect ratio of at least 2:1 and having a narrow dimension of less than 0.003 inches.

13. The adjustable stylet of claim 11 wherein said compression member is secured to said core wire proximate said blunt distal end of said core wire.

14. The adjustable stylet of claim 11 further comprising a rigid tube member operably positioned around said core wire between said proximal end of said compression member and said handle to transfer axial force applied by said handle to said compression member.

15. The adjustable stylet of claim 11 wherein said blunt end is comprised of a ball welded to said distal end of said core wire.

16. The adjustable stylet of claim 11 wherein said handle is slidable relative to said core wire.

17. The adjustable stylet of claim 11 wherein said handle includes a handle member secured to said core wire proximate said proximal end of the core wire and a moveable member operably engaged with said handle member such that said moveable member is axially moveable relative to said handle member within a distance determined by said handle member, said moveable member including a proximal portion extending distally beyond said handle member for operably engaging said proximal end of said compression member.

18. The adjustable stylet of claim 17 wherein said moveable member and said handle member include structure such that said moveable member is slidable relative to said handle member.

19. The adjustable stylet of claim 11 wherein said core wire comprises a wire having a uniform cross-sectional diameter.

20. The adjustable stylet of claim 11 wherein said core wire comprises a solid wire.

21. An adjustable stylet for use within a lumen of an intravascular device comprising:
- a core wire having a blunt distal end and a proximal end and having an outer diameter of less than 0.020 inches and a relatively uniform beam strength over an axial length of said core wire;
- a compression member having a distal end operably secured to said core wire and a proximal end axially movable along said core wire, said compression member comprising a flat wire space wound around at least a portion of said core wire to form a plurality of successive windings with a wide dimension of said flat wire oriented axially and an axial spacing between successive windings of said compression member;
- a handle operably mourned proximate said proximal end of said core wire, said handle axially movable to operably engage said proximal end of said compression member such that said axial spacing between at least a portion of said successive windings is adjusted by movement of said handle, whereby a stiffness of said stylet is adjusted by operation of said handle, and wherein said handle includes a handle member secured to said core wire proximate said proximal end of the core wire and a moveable member operably engaged with said handle member such that said moveable member is axially moveable relative to said handle member within a distance determined by said handle member, said moveable member including a proximal portion extending distally beyond said handle member for operably engaging said proximal end of said compression member, wherein at least one of said moveable member and said handle member includes structure to releasably position said moveable member relative to said handle member at multiple axial locations.

22. The adjustable stylet of claim 21 wherein said compression member is a flat stainless steel wire having an aspect ratio of at least 2:1 and having a narrow dimension of less than 0.003 inches.

23. The adjustable stylet of claim 21 wherein said compression member is secured to said core wire proximate said blunt distal end of said core wire.

24. The adjustable stylet of claim 21 further comprising a rigid tube member operably positioned around said core wire between said proximal end of said compression member and said handle to transfer axial force applied by said handle to said compression member.

25. The adjustable stylet of claim 21 wherein said blunt end is comprised of a ball welded to said distal end of said core wire.

26. The adjustable stylet of claim 21 wherein said handle is slidable relative to said core wire.

27. The adjustable stylet of claim 21 wherein said handle includes a handle member scoured to said core wire proximate said proximal end of the core wire and a moveable member operably engaged with said handle member such that said moveable member is axially moveable relative to said handle member within a distance determined by said handle member, said moveable member including a proximal portion extending distally beyond said handle member for operably engaging said proximal end of said compression member.

28. The adjustable stylet of claim 27 wherein said movable member and said handle member include structure such that said moveable member is slidable relative to said handle member.

29. The adjustable stylet of claim 21 wherein said core wire comprises a wire having a uniform cross-sectional diameter.

30. The adjustable stylet of claim 21 wherein said core wire comprises a solid wire.

31. An adjustable stylet for use within a lumen of an intravascular device comprising:
- a first core wire segment and a second core wire segment, each core wire segment having an outer diameter of less titan 0.020 inches and a relatively uniform beam strength over an axial length of said core wire segment, said relatively uniform beam strength providing sufficient rigidity for said axial length of said segment to maintain an arc when endpoints of said segment are maintained at a distance less than a length of said segment; and a compression member secured between adjacent ends of said first and second core wire segments, said compression member comprising a space wound wire with an axial spacing between successive windings of said compression member such that an axial force applied to at least one end of said compression member decreases said axial spacing between at least a portion of said successive windings.

32. The adjustable stylet of claim 31 wherein said compression member is a flat stainless steel wire having an aspect ratio of at least 2:1 and having a narrow dimension of less than 0.003 inches.

33. The adjustable stylet of claim 31 further comprising a cover tube surrounding at least a portion of said compression member and secured at only one end to one of said first and second core wire segments.

34. The adjustable stylet of claim 31 wherein said compression member is secured to said core wire proximate said blunt distal end of said core wire.

35. The adjustable stylet of claim 31 further comprising a rigid tube member operably positioned around said core wire between said proximal end of said compression member and a handle to transfer axial force applied by said handle to said compression member.

36. The adjustable stylet of claim 35 wherein said handle is slidable relative to said core wire.

37. The adjustable stylet of claim 15 wherein said handle includes a handle member secured to said core wire proximate said proximal end of the core wire and a moveable member operably engaged with said handle member such that said moveable member is axially moveable relative to said handle member within a distance determined by said handle member, said moveable member including a proximal portion extending distally beyond said handle member for operably engaging said proximal end or said compression member.

38. The adjustable stylet of claim 37 wherein said moveable member and said handle member include structure such that said moveable member is slidable relative to said handle member.

39. The adjustable stylet of claim 31 wherein said blunt end is comprised of a ball welded to said distal end of said core wire.

40. The adjustable stylet of claim 31, wherein said core wire comprises a wire having a uniform cross-sectional diameter.

41. The adjustable stylet of claim 31 wherein said core wire comprises a solid wire.

* * * * *